United States Patent
Sato

(10) Patent No.: US 9,031,201 B2
(45) Date of Patent: May 12, 2015

(54) X-RAY SOURCE, X-RAY IMAGING APPARATUS, AND X-RAY COMPUTED TOMOGRAPHY IMAGING SYSTEM

(75) Inventor: Genta Sato, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 317 days.

(21) Appl. No.: 13/808,194

(22) PCT Filed: Jun. 20, 2011

(86) PCT No.: PCT/JP2011/064607
§ 371 (c)(1),
(2), (4) Date: Jan. 3, 2013

(87) PCT Pub. No.: WO2012/005128
PCT Pub. Date: Jan. 12, 2012

(65) Prior Publication Data
US 2013/0108012 A1     May 2, 2013

(30) Foreign Application Priority Data
Jul. 5, 2010    (JP) ................................. 2010-153225

(51) Int. Cl.
*A61B 6/03*     (2006.01)
*H01J 35/00*    (2006.01)
(Continued)

(52) U.S. Cl.
CPC ........... *G01N 23/20075* (2013.01); *A61B 6/484* (2013.01); *G21K 1/067* (2013.01);
(Continued)

(58) Field of Classification Search
CPC .......... G01N 2021/8825; G01N 21/47; G01N 21/956; G01N 23/20075; G01N 21/4788; G01N 232/046; H01J 35/18; A61B 6/484; A61B 6/4035; G21K 1/067

USPC ........................... 378/4, 9, 19, 62, 70, 71, 140
See application file for complete search history.

(56) References Cited

U.S. PATENT DOCUMENTS 8,009,796 B2 *  8/2011  Popescu et al. .................. 378/19
2009/0154640 A1  6/2009  Baumann et al.
(Continued)

FOREIGN PATENT DOCUMENTS

JP     2005158474 A    6/2005
WO    2009104560 A1    8/2009

OTHER PUBLICATIONS

Momose et al., "Grating-Based X-ray Phase Imaging Using Multiline X-ray Source", Japanese Journal of Applied Physics 2009, vol. 48, p. 076512.

*Primary Examiner* — Nikita Wells
(74) *Attorney, Agent, or Firm* — Canon USA Inc. IP Division

(57) ABSTRACT

An X-ray imaging apparatus includes: an X-ray source including an electron source and a target, the target having a plurality of projections, each having an emitting surface; a diffraction grating configured to diffract X rays emitted from the X-ray source; and a detector configured to detect the X rays diffracted by the diffraction grating. Electron beams output from the electron source are incident on the emitting surfaces so that X rays are emitted from the emitting surfaces and are output to the diffraction grating. The X rays emitted from the emitting surfaces are diffracted by the diffraction grating so as to form a plurality of interference patterns. The projections are arranged such that bright portions of the interference patterns overlap each other and such that dark portions thereof overlap each other. Distances from the emitting surfaces to the diffraction grating are equal to each other.

14 Claims, 14 Drawing Sheets

(51) Int. Cl.
 *G21K 3/00* (2006.01)
 *G01N 23/223* (2006.01)
 *G01N 23/20* (2006.01)
 *G21K 1/06* (2006.01)
 *G01N 23/04* (2006.01)
 *H01J 35/18* (2006.01)
 *A61B 6/00* (2006.01)

(52) U.S. Cl.
 CPC ........ *G21K2207/005* (2013.01); *G01N 23/046* (2013.01); *H01J 35/18* (2013.01); *A61B 6/4021* (2013.01); *A61B 6/4035* (2013.01)

(56) References Cited

U.S. PATENT DOCUMENTS

| | | | |
|---|---|---|---|
| 2010/0080341 A1 | 4/2010 | Popescu et al. | |
| 2010/0246765 A1* | 9/2010 | Murakoshi et al. | 378/62 |
| 2010/0260315 A1* | 10/2010 | Sato et al. | 378/36 |
| 2010/0272235 A1* | 10/2010 | Takahashi | 378/62 |

* cited by examiner

US 9,031,201 B2

X-RAY SOURCE, X-RAY IMAGING APPARATUS, AND X-RAY COMPUTED TOMOGRAPHY IMAGING SYSTEM

TECHNICAL FIELD

The present invention relates to X-ray sources, X-ray imaging apparatuses, and X-ray computed tomography imaging systems.

BACKGROUND ART

The X-ray Talbot interference method is an X-ray imaging method utilizing the Talbot effect. With an application of X rays to a diffraction grating, interference patterns, which are called "self-images", are generated at a specific distance from the diffraction grating. When a specimen is placed between an X-ray source and a detector, the phase of the X rays is changed because of the presence of the specimen. Accordingly, the interference patterns having phase information concerning the specimen are detected, from which phase images of the specimen can be obtained.

It is necessary that X rays used in the Talbot interference method exhibit spatial-coherency. Spatial-coherency increases as the size of an X-ray source decreases. High-intensity X rays are also necessary in this interference method in order to increase the luminance of resulting images and to shorten the exposure time for a specimen.

Accordingly, in order to secure both X-ray spatial-coherency and X-ray intensity, a Talbot interference method performed by using an X-ray source which generates a plurality of narrow X-ray beams has been proposed.

NPL 1 discloses an X-ray source that generates a plurality of X-ray beams by irradiating a target provided with narrow grooves with electron beams. This X-ray source includes surfaces on the target from which X rays are emitted (hereinafter referred to as the "X-ray emitting surfaces" or more simply referred to as the "emitting surfaces"). By utilizing X-ray beams emitted in the oblique direction with respect to the X-ray emitting surfaces, the X-ray dosage per unit area is increased compared with a case where X-ray beams are emitted perpendicularly with respect to the X-ray emitting surfaces.

PTL 1 also discloses an X-ray source that can increase the X-ray dosage per unit area by irradiating a target provided with grooves with electron beams.

CITATION LIST

Patent Literature

PTL 1 Japanese Patent Laid-Open No. 2005-158474

Non Patent Literature

NPL 1 Japanese Journal of Applied Physics 2009, Vol. 48, p. 076512

SUMMARY OF INVENTION

Technical Problem

However, after studying the method disclosed in NPL 1, the present inventors have found that, in that method, the distances from the individual X-ray beam emitting surfaces on the target to the diffraction grating are inconsistent, which makes the interference patterns non-uniform and may impair the accurate imaging operation.

The present invention provides an X-ray imaging apparatus using an X-ray source which emits a plurality of X-ray beams so as to reduce the non-uniformity of interference patterns and to implement a more accurate imaging operation.

Solution to Problem

According to one aspect of the invention, there is provided an X-ray imaging apparatus including: an X-ray source including an electron source and a target, the target having a plurality of projections, each of the plurality of projections having an emitting surface; a diffraction grating configured to diffract X rays emitted from the X-ray source; and a detector configured to detect the X rays diffracted by the diffraction grating. Electron beams output from the electron source are incident on the emitting surfaces of the plurality of projections so that X rays are emitted from the emitting surfaces and are output to the diffraction grating. The X rays emitted from the emitting surfaces are diffracted by the diffraction grating so as to form a plurality of interference patterns. The plurality of projections are arranged such that bright portions of the plurality of interference patterns overlap each other and such that dark portions of the plurality of interference patterns overlap each other. Distances from the plurality of emitting surfaces to the diffraction grating are equal to each other.

Other aspects of the invention will be apparent from the embodiments described below.

Advantageous Effects of Invention

According to one aspect of the invention, there can be provided an X-ray imaging apparatus using an X-ray source which emits a plurality of X-ray beams so as to reduce a variation of the distances from X-ray emitting surfaces to a diffraction grating. Thus, it is possible to reduce the non-uniformity of interference patterns caused by a variation of the distances from the X-ray emitting surfaces to the diffraction grating.

DESCRIPTION OF EMBODIMENTS

Figure 1A:
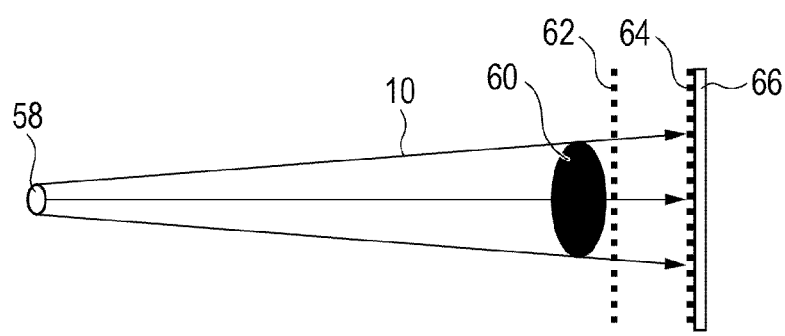
FIG. 1A is a schematic view illustrating an X-ray imaging apparatus according to a first embodiment of the invention.

Embodiments of the present invention are described in detail below with reference to the accompanying drawings. In the drawings, the same components are designated by like reference numerals, and an explanation thereof is given only once.

First Embodiment

FIG. 1A illustrates an example of the configuration of an X-ray imaging apparatus according to a first embodiment of the invention. The X-ray imaging apparatus shown in FIG. 1A includes an X-ray source 58, a diffraction grating 62 for diffracting X rays emitted from the X-ray source 58, a shielding grating 64 for blocking part of the X rays diffracted by the diffraction grating 62, and a detector 66 for detecting X rays passing through the shielding grating 64. The shielding grating 64 is disposed such that it is spaced apart from the diffraction grating 62 by a specific distance, which is referred to as the "Talbot distance".

By diffracting X rays 10 emitted from the X-ray source 58 with the diffraction grating 62, interference patterns, which are referred to as "Talbot self-images", reflecting the configuration of the diffraction grating 62 appear at a specific distance, which is called the "Talbot distance". When a specimen 60 is placed between the X-ray source 58 and the diffraction grating 62 or between the diffraction grating 62 and the shielding grating 64, the phase of the X rays 10 is shifted because of the presence of the specimen 60, thereby providing the interference patterns with information concerning a phase change of the specimen 60. Generally, since the pitch of the interference patterns is too small to be detected by the detector 66, in this embodiment, moire patterns are generated by using the shielding grating 64, and the generated moire patterns are detected by the detector 66. Accordingly, the shielding grating 64 which blocks part of the X rays 60 is disposed at a position at which interference patterns appear, i.e., at a position spaced apart from the diffraction grating 62 by the Talbot distance, and is caused to generate moire patterns. The moire patterns are detected by the detector 66. Then, image processing is performed on the detected moire patterns so as to obtain phase images of the specimen 60.

Figure 1B:
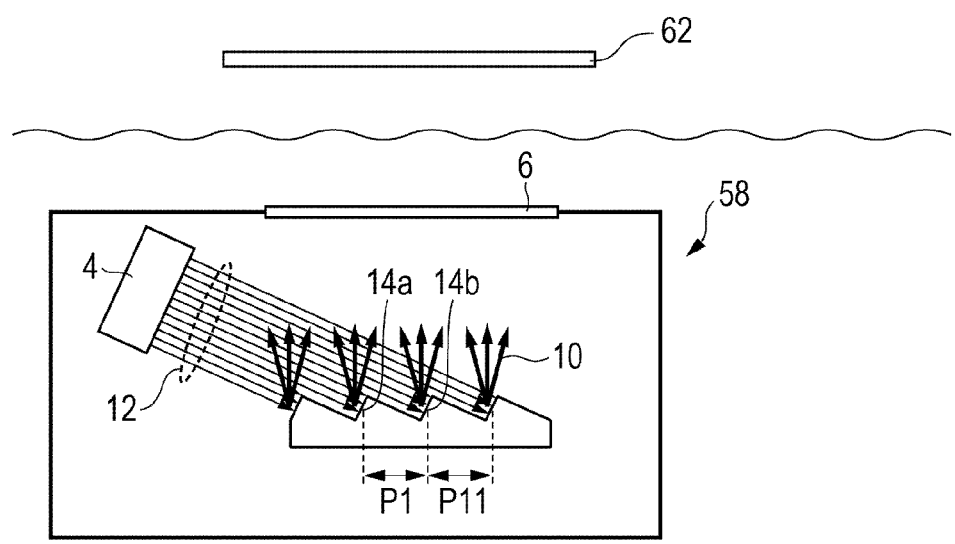
FIG. 1B is a schematic view illustrating an X-ray source according to the first embodiment of the invention.

FIG. 1B is an enlarged view of the X-ray source 58 shown in FIG. 1A. The X-ray source 58 includes an electron source 4, a target 2 on which electron beams 12 generated from the electron source 4 are incident, and an X-ray window 6 through which X rays generated in the target 2 are emitted to outside the X-ray source 58. The target 2 is provided with a plurality of emitting surfaces 14 (14a, 14b) on which the electron beams 12 generated from the electron source 4 are incident, and the emitting surfaces 14 (hereinafter referred to as the "first surfaces 14") are excited to generate the X rays 10, which are then emitted to outside the X-ray source 58 through the X-ray window 6. In this specification, the first surfaces are surfaces on which the electron beams are incident and from which the X rays are emitted and output to the diffraction grating. It is preferable that the angle between the first surfaces and the line perpendicular to the diffraction grating 62 (hereinafter simply referred to as the "perpendicular line") be greater than 0 degrees and not greater than 45 degrees. In the X-ray source 58, the first surfaces are surfaces on which the electron beams are incident and from which the X rays are emitted toward the X-ray window. It is preferable that the angle between the first surfaces and the straight line parallel with the line connecting the center of the target and the center of the X-ray window be greater than 0 degrees and not greater than 45 degrees.

Figure 2:
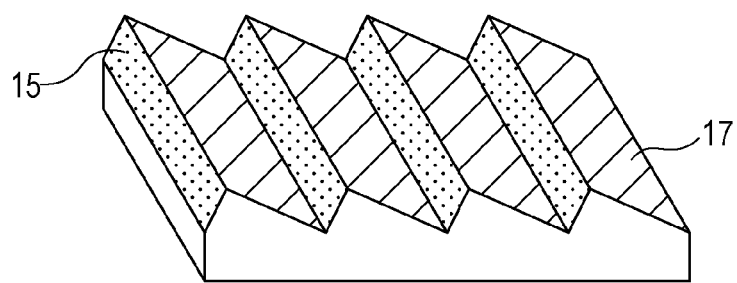
FIG. 2 is a schematic view illustrating a target according to the first embodiment of the invention.
Figure 3A:
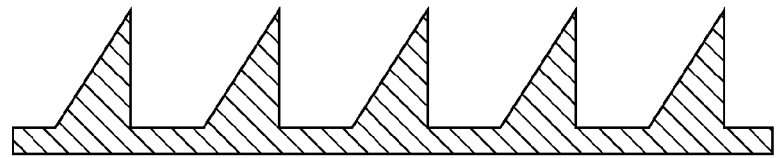
FIG. 3A is a sectional view schematically illustrating an example of the shape of a target according to the first embodiment of the invention.
Figure 3B:
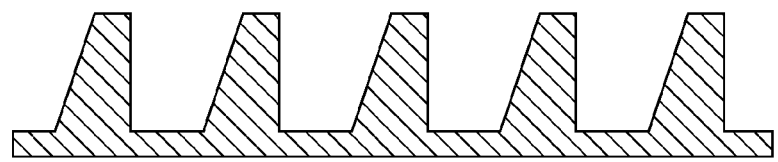
FIG. 3B is a sectional view schematically illustrating an example of the shape of the target according to the first embodiment of the invention.
Figure 3C:
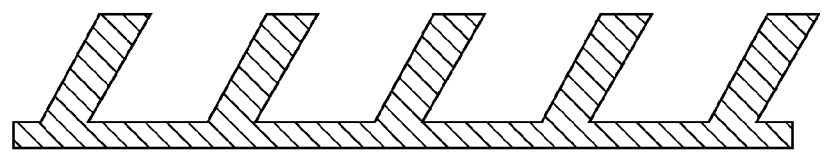
FIG. 3C is a sectional view schematically illustrating an example of the shape of the target according to the first embodiment of the invention.
Figure 3D:
FIG. 3D is a sectional view schematically illustrating an example of the shape of the target according to the first embodiment of the invention.

FIG. 2 is a schematic view illustrating the target 2 used in this embodiment. The target 2 is formed in a planar-like shape provided with projections thereon, and has a structure in which surfaces 15 including the first surfaces 14 and surfaces 17 including second surfaces are alternately repeated. The second surfaces in this embodiment are surfaces on which less electron beams are incident than on the first surfaces 14, i.e., the electron density of the second surfaces is lower than that of the first surfaces 14. The shape of the projections formed on the target 2 is not restricted to that shown in FIG. 2. FIGS. 3A through 3D illustrate variations of the shapes of the projections formed on the target 2. It is not necessary, as shown in FIG. 3A, that adjacent projections be in contact with each other. It is not necessary, as shown in FIGS. 3B and 3C, that projections be formed in an inverted V shape. As shown in FIG. 3D, projections may be formed in a curved shape.

The pitch P1 or P11 between the first surfaces 14 shown in FIG. 1B is the pitch of the intensity distribution of the X rays 10 emitted from the target 2. The pitch between the first surfaces 14 is the distance between the centers of the first surfaces 14, and the pitch of the intensity distribution of the X rays is the distance between the peaks of the X-ray intensity. The interference pattern formed by diffracting X rays 10 emitted from the first surface 14a with the diffraction grating 62 and the interference pattern formed by diffracting X rays 10 emitted from the first surface 14b with the diffraction grating 62 each include a bright portion and a dark portion. In the Talbot interference method, it is necessary that the bright portions of the plurality of interference patterns overlap each other to intensify each other on the shielding grating 64 and that the dark portions of the plurality of interference patterns overlap each other to intensify each other on the shielding grating 64. Accordingly, the pitches P1 and P11 should be set to satisfy such conditions. However, the bright portions of the interference patterns may overlap each other only partially and the dark portions of the interference patterns may overlap each other only partially. More specifically, part of the bright portion of the interference pattern formed by the X rays 10 emitted from the first surface 14a and part of the bright portion of the interference pattern formed by the X rays 10 emitted from the first surface 14b may overlap each other. The same applies to the dark portions of the interference patterns. As the overlapping area of the bright portions of interference patterns and the overlapping area of the dark portions of the interference patterns become larger, the imaging operation becomes more accurate. If the difference in pitch between the interference pattern formed by the X rays 10 emitted from the first surface 14a and the interference pattern formed by the X rays 10 emitted from the first surface 14b is ¼ the pitch of the interference patterns or smaller, such interference patterns can be used for the Talbot interference method. Accordingly, the difference among the interference patterns formed by the X rays 10 emitted from the plurality of first surfaces 14 (14a, 14b, . . . ) is preferably ¼ the pitch of the interference patterns or smaller. In order to implement a more accurate imaging operation, the difference among the interference patterns is more preferably ⅛ the pitch of the interference patterns or smaller, and is most preferably 1/20 the pitch of the interference patterns or smaller.

In order for the interference patterns to overlap each other to intensify each other, the pitch P1 or P11 preferably takes the value P0 expressed by the equation: $P0 = n \times Ps \times (L/d)$, where Ps is the pitch of the interference patterns in the Talbot self-image, L is the distance from the target 2 to the diffraction grating 62, d is the distance from the diffraction grating 62 to the interference patterns, and n is an arbitrary positive integer. In this embodiment, Ps is the pitch of the interference patterns on the shielding grating. Concerning the distance L, a detailed description is given later. The distance d is the distance from the center of the diffraction grating 62 to the center of the shielding grating 64 in this embodiment. The pitches between the first surfaces 14 in the same target 2 may be the same or may be different. That is, P1 and P11 may be different as long as they satisfy the conditions expressed by the above-described equation, and n may be different positive integers.

The first embodiment of the invention is described below by using the target 2 shown in FIG. 2 as an example. In the following description, the positional relationship between the surfaces 15 and 17 shown in FIG. 2 is maintained in the other cross sectional views, unless otherwise stated.

Figure 4A:
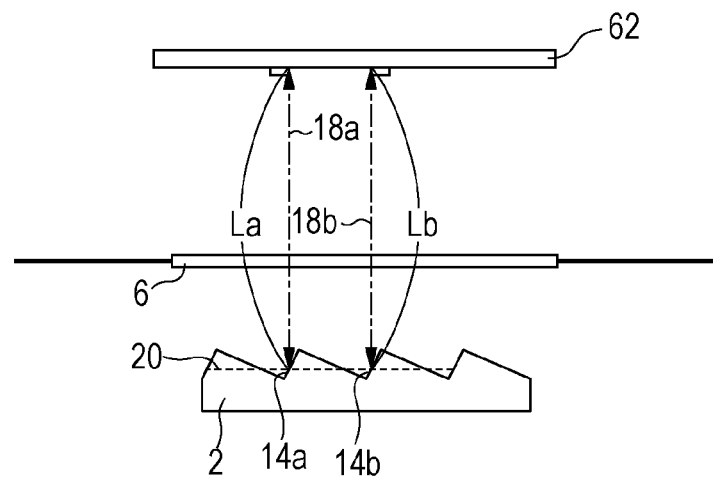
FIG. 4A is a schematic view illustrating the distance from emitting surfaces to a diffraction grating according to the first embodiment of the invention.

FIG. 4A is a schematic view illustrating the distance from the first surface 14 to the diffraction grating 62 according to the first embodiment of the invention. The lengths of perpendicular lines 18 (18a, 18b) drawn from the diffraction grating 62 to the centers of the first surfaces 14 are distances L (La, Lb) from the first surfaces 14 to the diffraction grating 62. The lengths of the perpendicular lines 18 are the lengths from the contact surface of the diffraction grating 62 to the centers of the first surfaces 14. In this case, the contact surface of the diffraction grating 62 is the surface that is in contact with the surface of the diffraction grating 62 which is most adjacent to the first surfaces 14. In this embodiment, the target 2 and the diffraction grating 62 are disposed so that the distance La from the first surface 14a to the diffraction grating 62 is equal to the distance Lb from the first surface 14b to the diffraction grating 62. The distances from the other first surfaces to the diffraction grating 62 are also equal to the distance La. A variation of the distances from the first surfaces to the diffraction grating 62 as much as an amount, for example, the height of the projections having the first surfaces 14 (hereinafter sometimes simply referred to as the "height of the projections") is negligible. That is, even if the distance La is different from the distance Lb by an amount, for example, the height of the projections, it is still considered that the distances La and Lb are equal to each other.

Figure 4B:
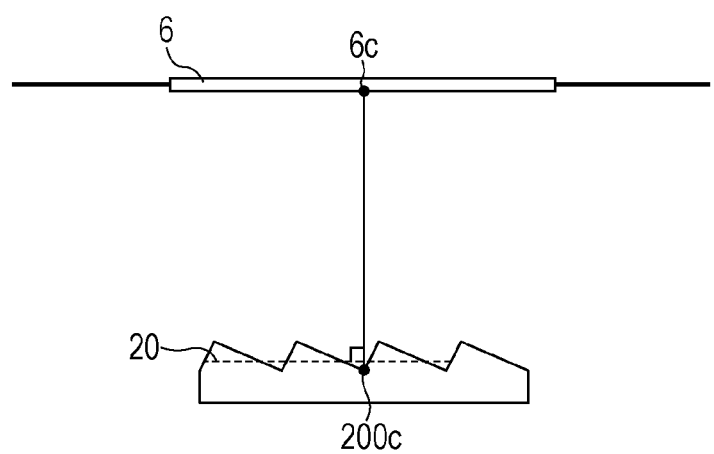
FIG. 4B is a schematic view illustrating the emitting surfaces and an X-ray window according to the first embodiment of the invention.

In the target 2, the surface formed by connecting the centers of the heights of the projections having the first surfaces 14 is set as a reference surface 20. If, as discussed above, the target 2 and the diffraction grating 62 are disposed so that the distances from the first surfaces 14 to the diffraction grating 62 are equal to each other, the reference surface 20 is parallel with the diffraction grating 62. However, it is not necessary that the reference surface 20 be exactly parallel with the diffraction grating 62. As discussed above, the distances La and Lb may be different by an amount, for example, the height of the projections. Thus, a variation as much as such an amount is negligible, in which case, it is still considered that the reference surface 20 and the diffraction grating 62 are parallel with each other. That is, it is sufficient that the distances L between the first surfaces 14 and the diffraction grating 62 be equal to each other in the overall four corners of the reference surface 20. In this case, too, an allowance as much as the above-described variation is given. As shown in FIG. 4B, the angle between the reference surface 20 and the line connecting a center 200c of an electron irradiation region, which is a region on the target 2 irradiated with electrons, and a center 6c of the X-ray window 6 is 90 degrees. In FIGS. 4A and 4B, the surface formed by connecting the centers of the heights of all the projections of the target 2 is set as the reference surface 20. However, it is not necessary to form the reference surface 20 by using all the projections on the target 2. The surface formed by connecting the centers of at least two projections may be set as the reference surface 20.

Figure 5A:
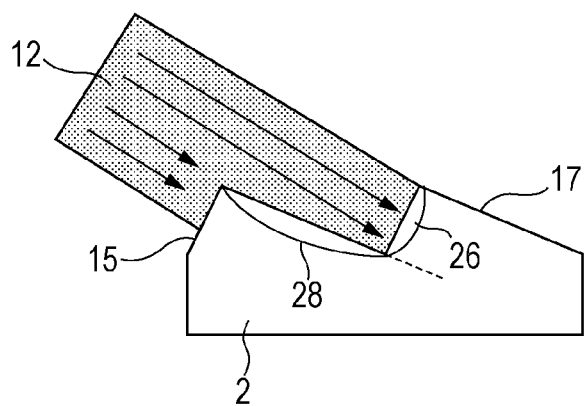
FIG. 5A is a schematic view illustrating the relationship between the configuration of a target and the density of electron beams incident on the target according to the first embodiment of the invention.
Figure 5B:
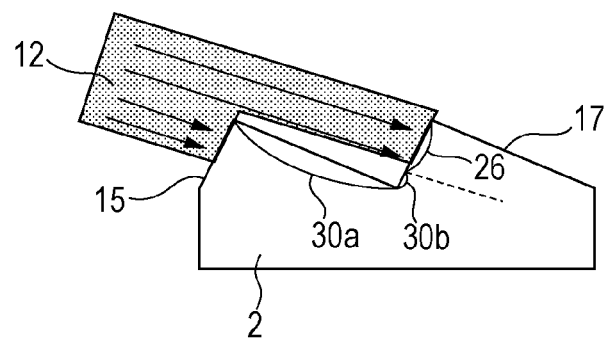
FIG. 5B is a schematic view illustrating the relationship between the configuration of a target and the density of electron beams incident on the target according to the first embodiment of the invention.

FIGS. 5A and 5B illustrate the configuration of the target 2 and the density of electron beams incident on the target 2. The electron beams 12 are emitted from the electron source 4 and are incident on the target 2. In this case, because of the structure of the projections of the target 2, more electron beams 12 are incident on an area 26 and less electron beams 12 are incident on an area 28. That is, the area 26 has a larger density of the electron beams 12 and the area 28 has a smaller density of the electron beams 12.

In this embodiment, as shown in FIG. 5A, the electron beams 12 are incident, substantially parallel with the surface 17, on the target 2. In this case, the first surface is the entirety of the surface 15. The surface 17 has a smaller density of the electron beams 12 than the surface 15, which is the first surface. Accordingly, the surface 17 serves as the second surface. The density of the electron beams 12 incident on the surface 15 is higher than that on the surface 17, and thus, the surface 15 is excited more intensely.

As shown in FIG. 5B, the angle between the electron beams 12 and the first surface may be greater than the angle formed by the surfaces 15 and 17. In this case, the electron beams 12 are not incident some areas of the target 2, such as areas 30 (30a, 30b), and the generation of X rays in the areas 30 is almost zero. In this case, on the surface 15, the area 30b does not form the first surface, and only the area 26 serves as the first surface. In this manner, a determination as to whether a certain surface serves as the first surface is made, not only by the configuration of a target, but also by the direction in which electron beams are incident.

The first embodiment of the invention is described below by assuming that the electron beams 12 are incident, as shown in FIG. 5A, substantially parallel with the surface 17, on the target 2. In this case, the entirety of the surface 15 serves as the first surface.

Figure 6:
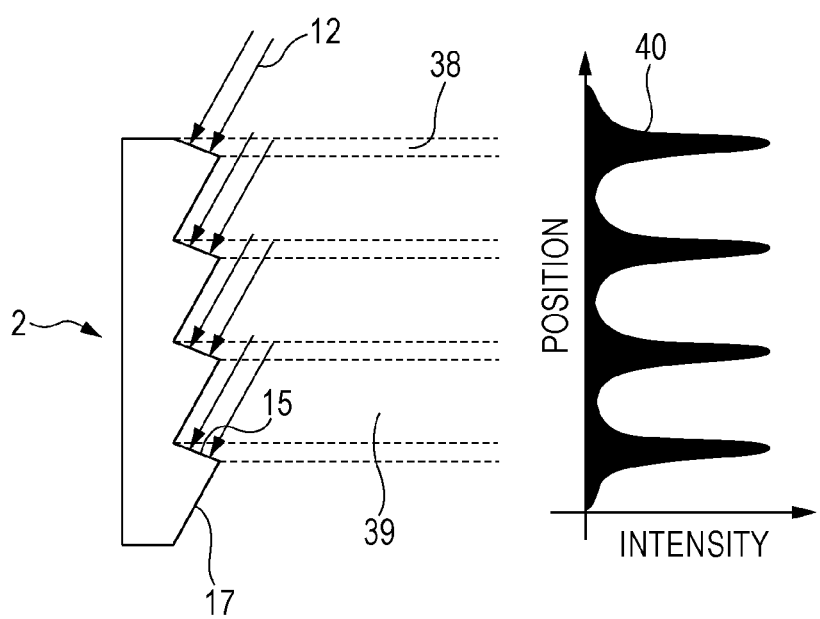
FIG. 6 is a schematic view illustrating the relationship between the density of electron beams incident on a target and the intensity of X rays emitted from the target according to the first embodiment of the invention.
Figure 7A:
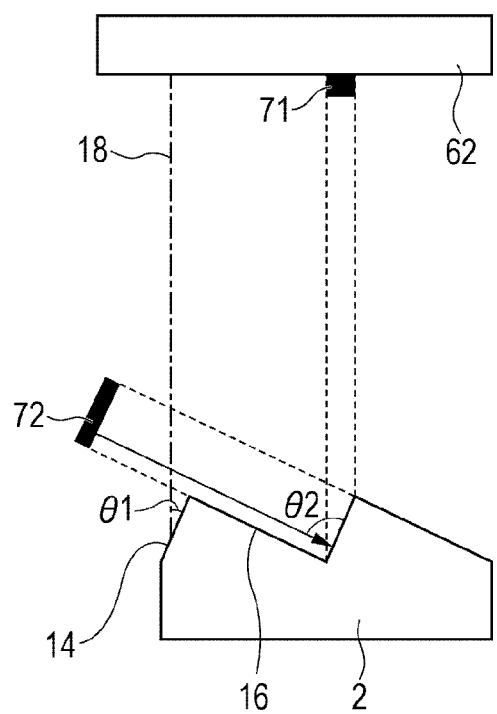
FIG. 7A is a schematic view illustrating the relationship between the configuration of a target and the intensity of X rays emitted from the target according to the first embodiment of the invention.
Figure 7B:
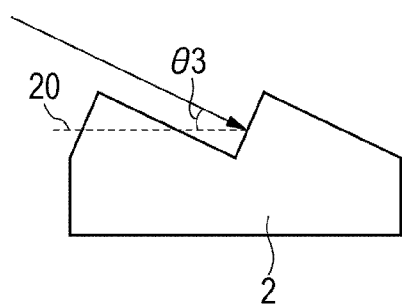
FIG. 7B is a schematic view illustrating the relationship between the configuration of a target and the intensity of X rays emitted from the target according to the first embodiment of the invention.

FIGS. 6, 7A, and 7B illustrate the relationship between the configuration of the target 2 and the spatial distribution between the density of electron beams incident on the target 2 and the intensity of X rays emitted from the target 2. In this embodiment, as described above, the electron beams 12 are principally incident on the surface 15 (first surface 14) and almost no electron beams 12 are incident on the surface 17 (second surface). Accordingly, X rays are emitted from the surface 15 but almost no X rays are emitted from the surface 17.

An intensity distribution 40 of the X rays measured in the vicinity of the target 2 reflects the structure of the surface of the target 2, and the intensity increases and decreases at the same pitch as the pitch (P1 or P11 shown in FIG. 1B) between the first surfaces 14. A width 38 of an area exhibiting a large intensity is determined by the width of a projected area 71 shown in FIG. 7, which is formed by projecting the first surface 14 on a plane parallel with the diffraction grating 62. That is, the half width of the peak of the X ray intensity is determined by the angle θ1 between the first surface 14 and the perpendicular line 18 with respect to the diffraction grating 62. As the angle θ1 approaches 0 degrees, the width of the projected area 71 decreases, and the half width of the peak of the X ray intensity in the intensity distribution 40 decreases. On the other hand, as the angle θ1 approaches 90 degrees, the width of the projected area 71 increases, and the half width of the peak of the X ray intensity in the intensity distribution 40 increases. If the first surface 14 is curved, the surface formed by connecting the four corners of the first surface 14 is assumed, and the angle θ1 formed by that surface and the perpendicular line 18 with respect to the diffraction grating 62 is considered. Hereinafter, when defining the angle between the first surface 14 and a line or a surface, if the first surface 14 is curved, the surface formed by connecting the four corners of the first surface 14 is similarly assumed, and then, the angle between the first surface 14 and a line or a surface is considered.

In this embodiment, the angle θ2 between the first surface 14 and the direction in which an electron beam 12 is incident on the first surface 14 is closer to 90 degrees than the angle θ1 formed between the first surface 14 and the perpendicular line 18 with respect to the diffraction grating 62. In this case, the projected area 71 formed by projecting the first surface 14 on a plane parallel with the diffraction grating 62 is smaller than a projected area 72 formed by projecting the first surface 14 on a plane perpendicular to the direction in which an electron beam 12 is incident. In this embodiment of the invention, the direction in which an electron beam 12 is incident on the first surface 14 is the direction in which an electron beam 12 travels straight and is incident on the first surface 14. If there is no object which deflects electron beams between the electron source 4 and the first surface 14, the direction in which an electron beam 12 is incident on the first surface 14 is considered to be the direction of the straight line connecting the center of the first surface 14 and the electron beam emitting portion of the electron source 4, which is the shortest distance. If the electron beams 12 are converged or diverged, for example, by the use of a lens to focus the electron beams 12 on the target 2, the average of the directions in which the electron beams 12 are incident on the first surface 14 is considered to be the direction in which the electron beams 12 are incident on the first surface 14.

The projected area 71 corresponds to a cross sectional area of X rays emitted from the first surface 14 to the diffraction grating 62, and the projected area 72 corresponds to a cross sectional area of an electron beam 12 incident on the first surface 14. The cross sectional area of the X rays emitted from the first surface 14 to the diffraction grating 62 is smaller than the cross sectional area of the electron beam 12 incident on the first surface 14. This means that the effect of increasing the X rays per unit area emitted from the first surface 14 is exhibited. This effect is more noticeable as the difference between the projected areas 71 and 72 is larger. In order to make the best use of this effect, it is desirable that the projected area 71 formed by projecting the first surface 14 on a plane parallel with the diffraction grating 62 be smaller than the projected area 72 formed by projecting the first surface 14 on a plane perpendicular to the direction in which the electron beam 12 is incident. Also, in order to make the difference between the intensity of the X rays emitted from the first surface 14 and that of the X rays emitted from the second surface 16 conspicuous, it is desirable that the projected area 71 formed by projecting the second surface 16 on a plane parallel with the diffraction grating 62 be larger than the projected area 72 formed by projecting the second surface 16 on a plane perpendicular to the direction in which the electron beam 12 is incident.

As described above, as the angle θ1 formed between the first surface 14 and the perpendicular line 18 with respect to the diffraction grating 62 approaches 0 degrees, the projected area 71 decreases, and on the other hand, as the angle θ2 formed between the first surface 14 and the electron beam 12 approaches 90 degrees, the projected area 72 increases. By considering this fact, the angle θ1 preferably ranges from 0 to 45 degrees, and the angle θ2 is preferably greater than 60 degrees and smaller than 120 degrees, and more preferably ranges from 80 to 100 degrees.

However, if the angle θ1 is 0 degrees, i.e., if the first surface 14 is perpendicular to the diffraction grating 62, because of the fine undulating shape on the first surface 14, X rays generated in the first surface 14 are absorbed by the first surface 14 itself, i.e., the so-called "heel effect" is exhibited, thereby decreasing the intensity of the X rays emitted from the first surface 14. By considering this fact, the angle θ1 between the first surface 14 and the perpendicular line 18 with respect to the diffraction grating 62 is preferably greater than 0 degrees, and more preferably 3 degrees or greater.

When the angle θ1 is greater than 0 degrees and is not greater than 45 degrees and when the angle θ2 is greater than 60 degrees and smaller than 120 degrees, the angle θ3 formed between the electron beam 12 and the reference surface 20 is greater than 0 degrees and smaller than 75 degrees. Also, the reference surface 20 is parallel with the diffraction grating 62. Accordingly, when the angle θ1 is greater than 0 degrees and is not greater than 45 degrees, the angle formed between the reference surface 20 and the first surface 14 is 45 degrees or greater and is smaller than 90 degrees.

Figure 8A:
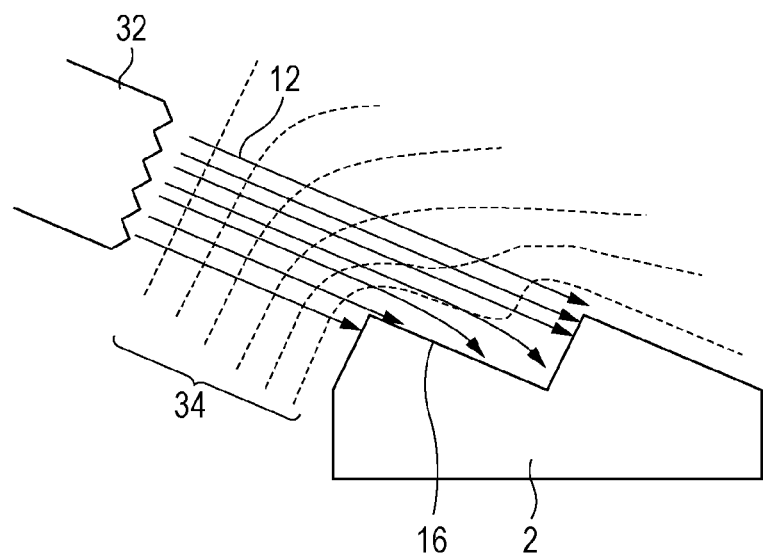
FIG. 8A is a schematic view illustrating an electron source according to the first embodiment of the invention.
Figure 8B:
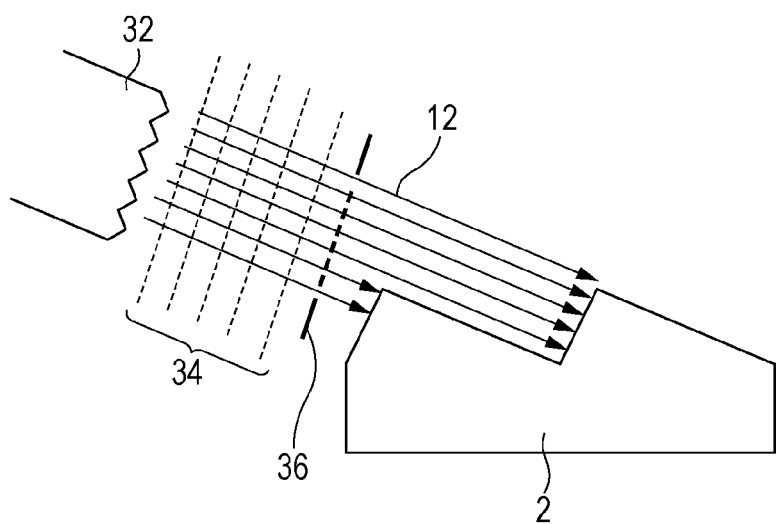
FIG. 8B is a schematic view illustrating an electron source according to the first embodiment of the invention.

The provision of an anode for the electron source 4 is not necessary, but is desirable. FIGS. 8A and 8B illustrate the action of the electron source 4 and the target 2. The electron beams 12 travel along an electric field. It is known that on the surface of a conductor, an electric field is connected in the direction of a normal line of the surface of the conductor. FIG. 8A illustrates the action of the electron source 4 without an anode and the target 2. For the electron source 4 without an anode, with an application of a voltage higher than a cathode 32, which serves as an anode, to the target 2, the target 2 is caused to generate X rays. In the vicinity of the surface of the target 2, an equipotential surface 34 is generated in accordance with the configuration of the target 2, and an electric field reflecting the configuration of the target 2 is generated. Accordingly, the electron beams 12 directed from the cathode 32 to the first surface 14 curve in the vicinity of the target 2, and are also incident on the second surface 16.

FIG. 8B illustrates the action of the electron source 4 provided with an anode 36 as well as the cathode 32 and the target 2. The anode 36 may take any configuration as long as it can transmit the electron beams 12, for example, a net-like, thin-film, or porous anode 36 may be used. Electrons generated in the cathode 32 are accelerated between the cathode 32 and the anode 36. By setting the anode 36 and the target 2 to be equipotential, an electric field is not generated between the anode 36 and the target 2. Accordingly, the electron beams 12 passing through the anode 36 can be directly incident on the target 2 regardless of the structure of the target 2.

The target 2 may be formed of a plurality of band-like partial targets. One target may be formed by arranging a plurality of partial targets in the direction perpendicular to the direction in which the first surfaces are arranged in each of the plurality of partial targets.

Figure 9A:
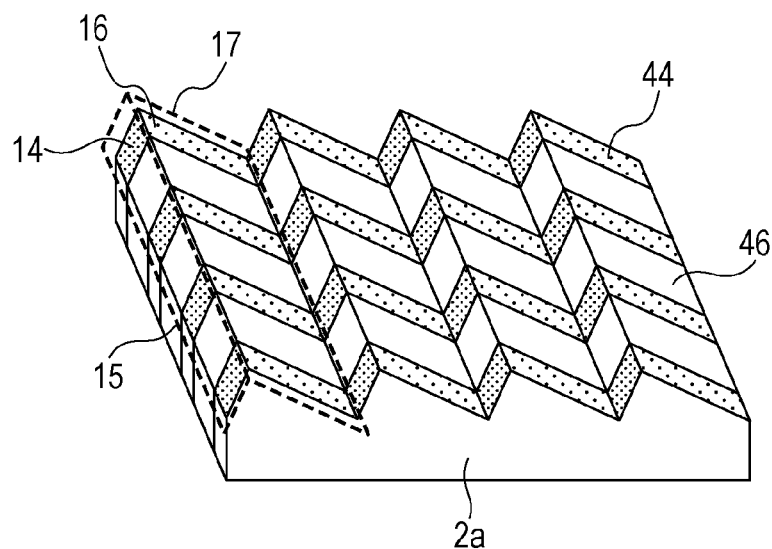
FIG. 9A is a perspective view schematically illustrating a first modification made to a target according to the first embodiment of the invention.
Figure 9B:
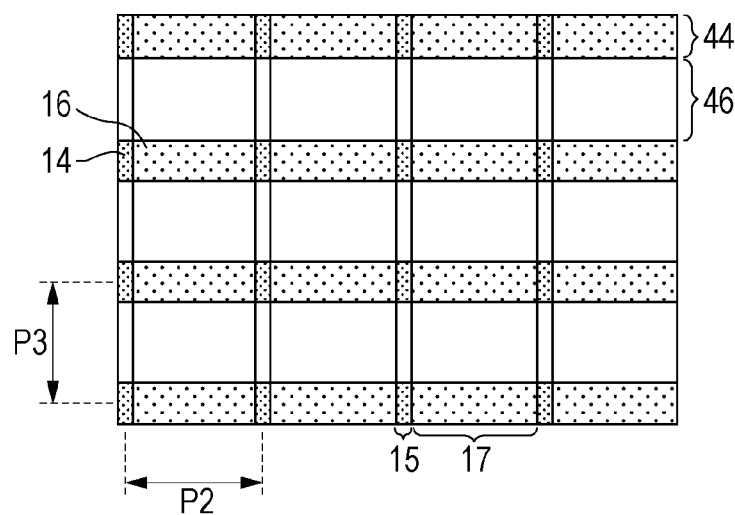
FIG. 9B is a plan view schematically illustrating the first modification made to a target according to the first embodiment of the invention.

If a target is configured by a combination of partial targets having surfaces made of different materials, X ray beams emitting from such a target can be provided with a two-dimensional arrangement. FIGS. 9A and 9B are respectively a perspective view and a plan view schematically illustrating a single target 2a formed by band-like partial targets made of different materials. The target 2a is formed by alternately connecting first partial targets 44 and second partial targets 46. The first partial targets 44 are made of heavy metal that converts electron beam energy into X rays, while the second partial targets 46 are made of light metal whose conversion rate for converting the electron beam energy into X rays is lower than the first partial targets 44. The heavy metal used for the first partial targets 44 includes molybdenum, tungsten, and silver. The light metal used for the second partial targets 46 includes carbon, aluminum, and beryllium. With an application of electron beams to this light metal, substantially no X rays are generated from the light metal, i.e., substantially no X rays are generated from the second partial targets 46. Thus, with an application of the electron beams 12 in parallel with the surface 17, the surface 15 is excited, whereby X rays are not substantially generated, except from the first surface 14, which is the surface 15 on the first partial targets 44. As a result, the X rays emitted from the target 2a have a two-dimensional intensity distribution. In this case, the X-ray beams have axes which are parallel with and perpendicular to the direction in which the surfaces 15 are arranged. The pitches P2 and P3 take values expressed by the above-described equation n×Ps×(L/d) so that the interference patterns formed by the X rays emitted from the first surfaces 14 in the target 2a intensify each other. The pitches P2 and P3 may be the same or may be different. Since the second partial targets 46 do not substantially contribute to the generation of X rays, the configuration of the second partial targets 46 is not particularly restricted.

Figure 10A:
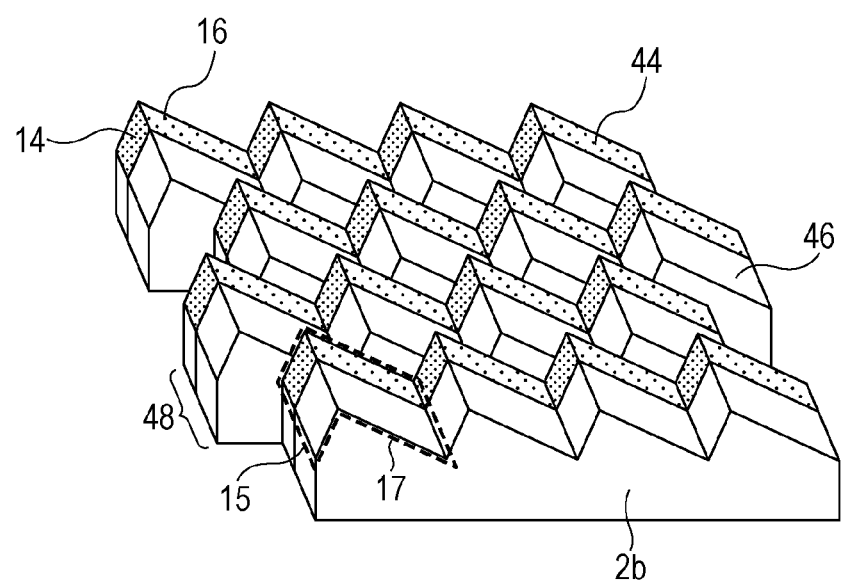
FIG. 10A is a perspective view schematically illustrating a second modification made to a target according to the first embodiment of the invention.
Figure 10B:
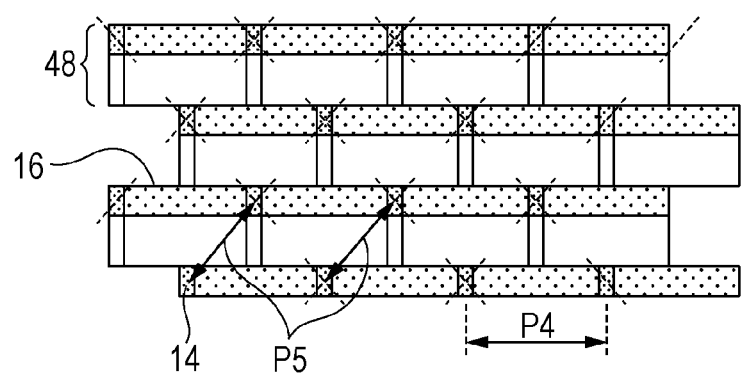
FIG. 10B is a plan view schematically illustrating the second modification made to a target according to the first embodiment of the invention.

Even if a target is formed by discontinuously arranging the first surfaces 14 perpendicular to the direction in which the surfaces 15 are arranged, X-ray beams emitted from the target can be provided with a two-dimensional arrangement. In this case, the direction in which the first surfaces 14 are arranged in the overall target is oblique to the direction in which the first partial targets are arranged, and intersects with the direction in which the emitting surfaces are arranged in each of the first partial targets and also intersects with the direction in which the first partial targets are arranged. FIGS. 10A and 10B are respectively a perspective view and a plan view schematically illustrating a target 2b formed by combining partial targets made of different materials and by discontinuously arranging the first surfaces 14. In the target 2b shown in FIG. 10A, a pair of a first partial target 44 and a second partial target 46 form one region 48. Adjacent regions 48 are displaced from each other by half the pitch P4 in the direction in which the surfaces 15 of the partial targets are arranged. With an application of the electron beams 12 in parallel with the surfaces 17, the first surfaces 14 are excited, whereby substantially no X rays are generated, except from the first surfaces 14, as in the target 2a shown in FIG. 9A. As a result, X rays having a two-dimensional intensity distribution are generated from the target 2a. In this case, the axes of the first surfaces 14 of the X-ray beams are inclined by 45 degrees with respect to the direction in which the surfaces 15 are arranged. The pitch P5 takes a value expressed by the equation n×Ps×(L/d) so that the interference patterns formed by the X rays emitted from the first surfaces 14 in the target 2b shown in FIG. 10A intensify each other. The pitch P5 is the pitch between the most adjacent first surfaces 14 in the target 2b.

The displacement between the adjacent regions 48 in the direction in which the surfaces 15 are arranged does not have to be the half the pitch P4. However, it is necessary that the bright portions of the interference patterns formed by diffracting the plurality of X-ray beams with the diffraction grating 62 overlap each other, and also, the dark portions thereof overlap each other.

Figure 14:
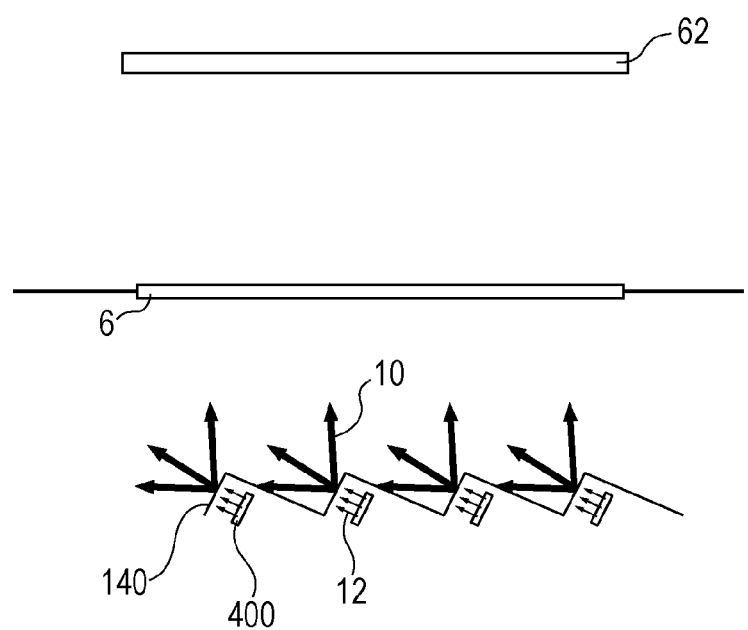
FIG. 14 is a schematic view illustrating a third modification made to a target according to the first embodiment of the invention.

A plurality of electron sources may be used, in which case, electron beams emitted from the plurality of electron sources are incident on the first surfaces. The use of a plurality of electron sources implements fine control of electron beams. Additionally, instead of a reflection-type target, a transmitting-type target may be used. FIG. 14 illustrates an X-ray source provided with a transmitting-type target and one electron source provided for each first surface. In the X-ray source shown in FIG. 14, electron beams 12 emitted from an electron source 400 are incident on a first surface 140 of the transmitting-type target, and then, X rays 10 are generated. The generated X rays 10 are emitted to outside the X-ray source through an X-ray window 6 and are diffracted by the diffraction grating 62 so as to form interference patterns. Generally, however, the cooling efficiency is higher by the use of reflection-type targets than by the use of transmitting-type targets, and an increase in the temperature of the targets can be suppressed, thereby increasing input power. Thus, the use of reflection-type targets is more desirable.

Second Embodiment

A second embodiment of the invention is described below with reference to FIGS. 11 through 13B.

The second embodiment is different from the first embodiment in that the target of an X-ray source is of a rotary type. The components other than the X-ray source are similar to those of the first embodiment, and an explanation thereof is thus omitted.

Figure 11:
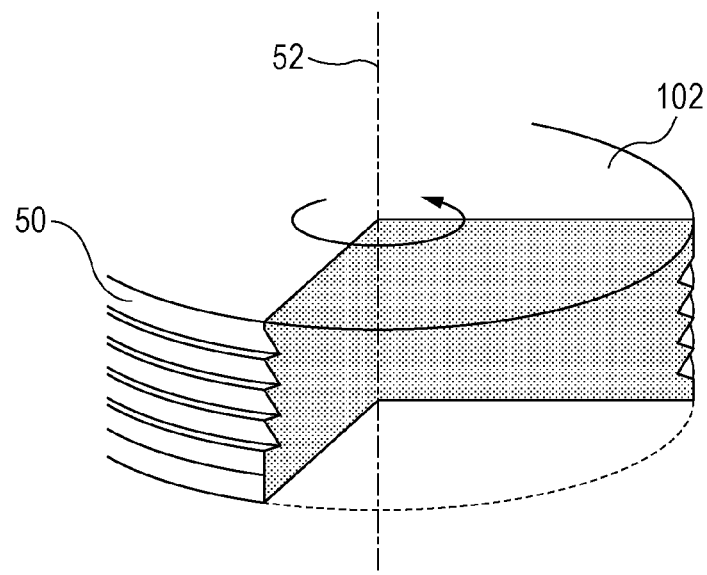
FIG. 11 is a schematic view illustrating a target according to a second embodiment of the invention.

FIG. 11 is a schematic view illustrating a target 102 used in the second embodiment. The target 102 has a cylindrical shape and is rotatable about an axis of symmetry 52. The diffraction grating 62 is disposed in parallel with the axis of symmetry 52. The target 102 has projections at lateral sides thereof in parallel with the axis of symmetry 52.

Figure 12A:
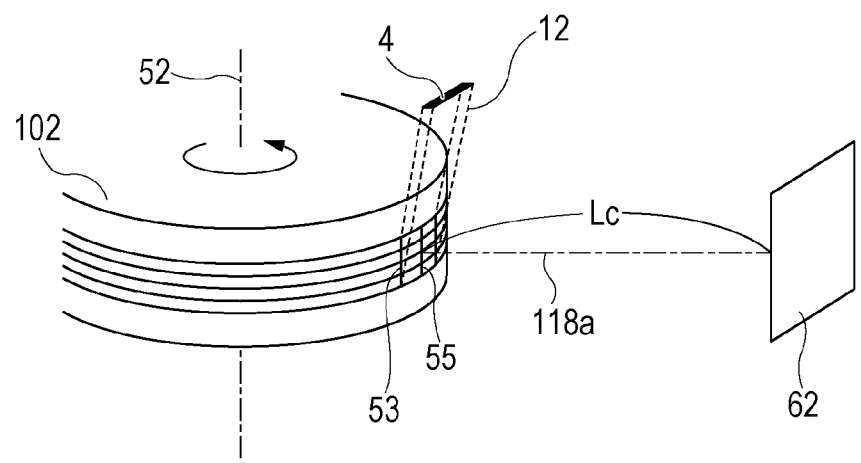
FIG. 12A is a schematic view illustrating an X-ray generating method according to the second embodiment of the invention.

FIG. 12A is a schematic view illustrating an X-ray generating method of the second embodiment. The relationship between the irradiation direction of the electron beams 12 and the surfaces of the projections and the relationship between the emitting direction of the X rays 10 and the intensity distribution are the same as those of the first embodiment.

The electron beams 12 are applied to a limited electron-beam irradiation region 53 (hereinafter referred to as the "irradiation region") on the lateral surface of the cylindrical target 102, and X rays are emitted only from the irradiation region 53. By rotating the target 102 about the axis of symmetry 52, electron beam heat is distributed on the entire lateral surface of the cylindrical target 102, thereby making it possible to suppress an increase in the temperature of the target 102, which would otherwise be caused by the irradiation of electron beams. Thus, input power can be increased compared to a case where a fixed-type target is used.

Figure 12B:
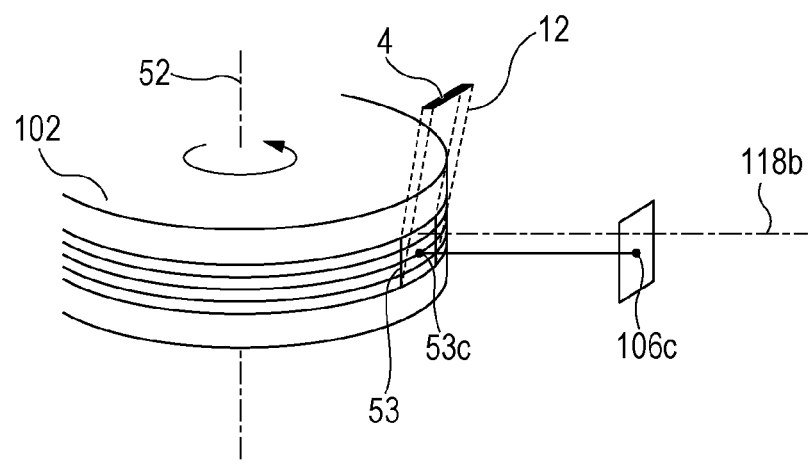
FIG. 12B is a schematic view illustrating an X-ray generating method according to the second embodiment of the invention.

The distance from the first surface 14 to the diffraction grating 62 is described below with reference to FIGS. 12A and 12B. A center line 55 is drawn on the irradiation region 53 in the direction parallel with the first surface 14. A plurality of first surfaces 14 are disposed on the center line 55. A perpendicular line 118a is drawn from the diffraction grating 62 to the center of the first surfaces 14 disposed on the center line 55. The length of the perpendicular line 118a is set to be the distance Lc between the first surfaces 14 and the diffraction grating 62. As in the first embodiment, the length of the perpendicular line 118a is the length from the contact surface of the diffraction grating 62 to the center of the first surfaces 14, and the distances from the diffraction grating 62 to the plurality of first surfaces 14 disposed on the center line 55 are equal to the distance Lc. Even by rotating the target 102 about the axis of symmetry 52, the irradiation region 53 is fixed with respect to the diffraction grating 62 and the target 102, whereby the distances from the diffraction grating 62 to the first surfaces 14 that generate X rays are kept constant.

The reference surface in this embodiment is the surface formed by connecting the centers of the heights of the projections on the center line 55. As in the first embodiment, the line connecting a center 53c of the irradiation region 53 and a center 106c of the X-ray window forms an angle of 90 degrees with respect to the reference surface, and is parallel with the perpendicular line 118b.

Figure 13A:
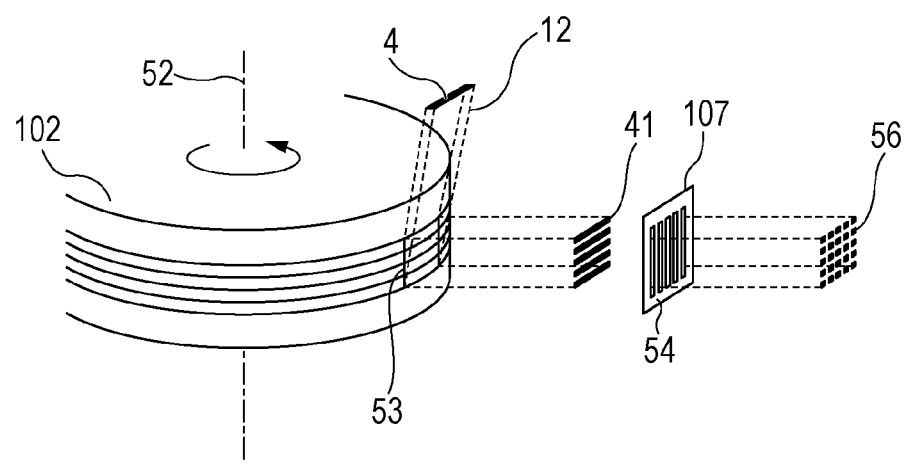
FIG. 13A is a schematic view illustrating a modification made to an X-ray source according to the second embodiment of the invention.
Figure 13B:
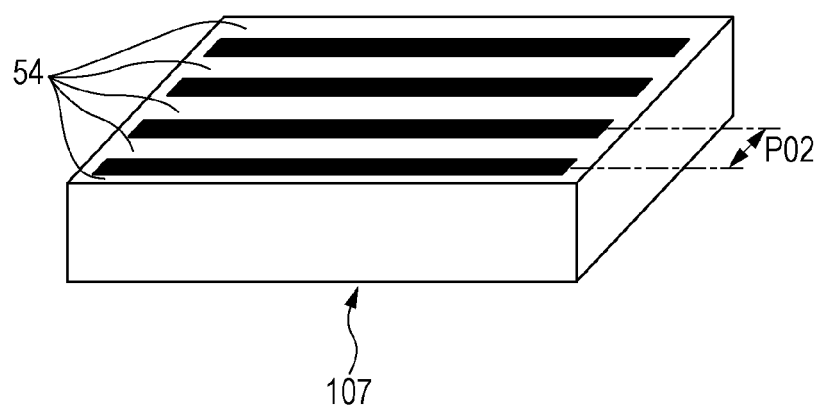
FIG. 13B is a schematic view illustrating an X-ray window of the modification made to the X-ray source according to the second embodiment of the invention.

As shown in FIG. 13A, if the irradiation region 53 is a quadrilateral, X rays emitted from the target 102 exhibit a linear intensity distribution, such as the linear arrangement designated by reference numeral 41. The X rays emitted from the target 102 may be directly extracted, or may be converted into a second-dimensional arrangement as shown in FIG. 13A. In the X-ray source, X-ray shielding members 54 for blocking X rays in a band-like shape are provided for the X-ray window 107. FIG. 13B is a perspective view illustrating the X-ray window 107. The X-ray shielding members 54 are arranged in the direction orthogonal to the direction in which the first surfaces 14 are arranged. Accordingly, after the X rays 41 pass through the X-ray window 107, an intensity distribution 56 is obtained. It is necessary that the bright portions of interference patterns formed by diffracting a plurality of X-ray beams with the diffraction grating 62 overlap each other and that the dark portions of the interference patterns also overlap each other. In order to satisfy such conditions, the pitch P02 between the X-ray shielding members 54 is expressed by the equation: $n \times Ps \times (L2/d)$, where Ps is the pitch of the interference patterns in the Talbot self-image obtained by the diffraction grating 62 and arranged on the shielding grating 64, L2 is the distance from the X-ray window 107 to the diffraction grating 62, d is the distance from the diffraction grating 62 to the shielding grating 64, and n is an arbitrary positive integer.

The method for converting X-ray beams into a two-dimensional arrangement by using the X-ray window 107 provided with the X-ray shielding members 54 is also applicable to the use of a fixed-type target, such as that of the first exemplary embodiment.

More specific examples of the first and second embodiments are described below.

First Example

In a first example, the first embodiment is more specifically explained.

In the first example, a target 2 having projections is formed by cutting V-shaped grooves on the surface of a molybdenum plate. The projections are formed such that the angle $\theta 1$ between the first surface 14 and the perpendicular line 18 with respect to the diffraction grating 62 is 6 degrees and the angle between the second surface 16 and the perpendicular line 18 with respect to the diffraction grating 62 is 84 degrees. The angle between the first surface 14 and the second surface 16 is 90 degrees.

The pitch between the first surfaces 14 is set such that interference patterns of X rays emitted from the plurality of first surfaces 14 overlap each other. In this example, the pitch Ps of the interference patterns of the self-image is 2 µm, L is 1.765 m, and d is 27.77 mm. Accordingly, in order to satisfy the equation of $n \times Ps \times (L/d)$, n is set to be 1, and the pitch between the first surfaces 14 is set to be 127 µm. The projections of the target 2 are formed with the above-described angles, distances, and pitches, and the height of the projections is 13.2 µm.

The electron source 4 is disposed so that the electron beams 12 are incident in parallel with the second surfaces 16 of the target 2. In this case, the electron beams 12 are incident perpendicular to the first surfaces 14. The electron source 4 includes a cathode 32 using a tungsten filament and an anode 36 made of a tungsten mesh.

The anode 36 and the target 2 are set to be 0 V, and the cathode 32 is set to be –30 kV. Electrons generated by heating the filament of the cathode 32 are accelerated with an electric field between the cathode 32 and the anode 36, thereby generating the electron beams 12. Since an electric field is not generated between the anode 36 and the target 2, the electron beams 12 are incident in parallel with the second surfaces 16 of the target 2, and accordingly, only the first surfaces 14 are excited by the electron beams 12. The X rays 10 are isotropically generated from the excited first surfaces 14 and are emitted to outside the X-ray source 58 through a beryllium X-ray window 6 having a thickness of 1 mm, which is disposed toward the diffraction grating 62.

As discussed above, in this example, the angle between the first surface 14 and the perpendicular line 18 with respect to the diffraction grating 62 is 6 degrees, and the angle between an electron beam 12 and the first surfaces 14 is 90 degrees. In this case, the area of the first surface 14 as viewed from the perpendicular line with respect to the diffraction grating 62 is about 1/10 the area of the first surface 14 as viewed from the electron beams 12 incident on the first surface 14. As a result, the intensity of X rays per unit area is increased. Since the second surfaces 16 are hardly excited and since the intensity of the X rays per unit area emitted from the first surfaces 14 is increased, the X rays emitted from the first surfaces 14 exhibit a linear intensity distribution. In the linear arrangement of the intensity distribution, the width of the X rays 10 in the direction in which the first surfaces 14 are arranged is about 1.3 μm.

Since the direction in which the X rays 10 are arranged match the direction in which the diffraction grating 62 is arranged, the X rays 10 exhibit coherence. Thus, the intensity of the interference patterns of the X rays 10 emitted from the plurality of first surfaces 14 is increased. The resulting Talbot self-images are detected, and phase information of the specimen 60 placed in front of the diffraction grating 62 is obtained.

Second Example

In a second example, an application of the second embodiment to an X-ray computed tomography imaging system is more specifically described.

In the second example, the target 102 has a molybdenum cylindrical shape. The diameter and the height of the cylinder are 10 cm and 2 cm, respectively. Projections are formed on the lateral surface of the target 102 by circumferentially cutting grooves. The angles of the projections and the pitches between the first surfaces and the depths of the first surfaces are similar to those of the first example.

In the plane including the axis of symmetry 52 of the target 102 and the perpendicular line 18 with respect to the diffraction grating 62, the electron source 4 is disposed so that the electron beams 12 are incident perpendicularly on the first surfaces 14. As in the first example, the electron source 4 includes a cathode 32 using a tungsten filament and an anode 36 made of a tungsten mesh. As in the first example, the target 102 is excited by being irradiated with the electron beams 12 emitted from the electron source 4, thereby generating X rays 10. While applying the electron beams 12 to the target 102, the target 102 is rotated about the axis of symmetry 52 at about 6000 rpm. The X rays 10 are emitted to outside the X-ray source 58 through the beryllium X-ray window 106 having a thickness of 1 mm, which is disposed toward the diffraction grating 62. Phase images concerning the specimen 60 are obtained from a plurality of directions by utilizing the Talbot interferences. Then, computer processing is performed on the phase images, thereby obtaining a tomographic image of the specimen 60.

In the above-described embodiments of the invention, in the X-ray imaging apparatus, the shielding grating 64 and the detector 66 are independently disposed. However, the shielding grating 64 and the detector 66 may be integrally formed. Any types of shielding grating and detector may be used as long as the shielding grating can form moire patterns which overlap self-images of the diffraction grating 62 and the detector can detect the moire patterns. For example, the detector disclosed in Japanese Patent Laid-Open No. 2008-224661 may be used. If the shielding grating 64 and the detector 66 are integrally formed, the distance from the member for forming moire patterns to the diffraction grating 62 is set to be d. Alternatively, if self-images can be directly detected by the detector, it is not necessary that moire patterns be formed, and accordingly, the use of a shielding grating is not necessary. In order to directly detect self-images with the detector 66, the pitch of self-images is increased by increasing the pitch of the diffraction grating 62 or the distance from the X-ray source 58 to the diffraction grating 62, or a high-resolution detector may be used. If self-images are directly detected, it is necessary that the bright portions of the self-images overlap each other so as to intensify each other on the detection surface of the detector and the dark portions of the self-images overlap each other so as to intensify each other on the detection surface of the detector. Accordingly, when self-images are directly detected, in the above-described equations: $P0=n \times Ps \times (L/d)$ and $P02=n \times Ps \times (L2/d)$, d is the distance from the center of the diffraction grating to the center of the detection surface of the detector, and Ps is the pitch of the interference patterns on the detector.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-153225, filed Jul. 5, 2010, which is hereby incorporated by reference herein in its entirety.

INDUSTRIAL APPLICABILITY

The present invention is applicable to an X-ray imaging apparatus that obtains phase images of a specimen with the use of a phase change generated by allowing the specimen to transmit X rays.

REFERENCE SIGNS LIST 2 target
4 electron source
10 X ray
12 electron beam
14 emitting surface
62 diffraction grating
64 shielding grating
66 detector
P1 through P5 pitch between emitting surfaces
P02 pitch between X-ray shielding members
P11 pitch between emitting surfaces

The invention claimed is:

1. An X-ray imaging apparatus comprising:
an X-ray source including an electron source and a target, the target having a plurality of projections, each of the plurality of projections having an emitting surface;
a diffraction grating configured to diffract X rays emitted from the X-ray source; and
a detector configured to detect the X rays diffracted by the diffraction grating,
wherein electron beams output from the electron source are incident on the emitting surfaces of the plurality of projections so that X rays are emitted from the emitting surfaces and are output to the diffraction grating, the X rays emitted from the emitting surfaces are diffracted by the diffraction grating so as to form a plurality of interference patterns, the plurality of projections are arranged such that bright portions of the plurality of interference patterns overlap each other and such that dark portions of the plurality of interference patterns overlap each other, and distances from the plurality of emitting surfaces to the diffraction grating are equal to each other.

2. The X-ray imaging apparatus according to claim 1, wherein the target is arranged such that a reference surface formed by connecting the centers of heights of the plurality of projections having the emitting surfaces is parallel with the diffraction grating.

3. The X-ray imaging apparatus according to claim 1, wherein an angle between each of the plurality of emitting surfaces and a line perpendicular to the diffraction grating is greater than 0 degrees and is not greater than 45 degrees.

4. The X-ray imaging apparatus according to claim 1, wherein the electron beams are incident on the target with an angle of greater than 0 degrees and smaller than 75 degrees with respect to a reference surface formed by connecting the centers of heights of the plurality of projections having the emitting surfaces.

5. The X-ray imaging apparatus according to claim 1, wherein the target includes a plurality of second surfaces, and the density of the electron beams incident on the plurality of emitting surfaces is higher than the density of the electron beams incident on the plurality of second surfaces.

6. The X-ray imaging apparatus according to claim 1, wherein the target is a reflection-type target.

7. The X-ray imaging apparatus according to claim 1, wherein the plurality of emitting surfaces are arranged on the target with a pitch P0 between the emitting surfaces expressed by an equation: $P0=n \times Ps \times (L/d)$, where n is an arbitrary positive integer, Ps is the pitch of the interference patterns formed with the diffraction grating, L is the distance from the target to the diffraction grating, and d is the distance from the diffraction grating to the interference patterns.

8. The X-ray imaging apparatus according to claim 1, wherein:
the X-ray source includes an X-ray window through which the X rays generated from the X-ray source are emitted to outside the X-ray source, the X-ray window including X-ray shielding members configured to block the X rays generated from the X-ray source; and
the X-ray shielding members are arranged in the X-ray window with a pitch P02 between the X-ray shielding members expressed by an equation: $P02=n \times Ps \times (L2/d)$, where n is an arbitrary positive integer, Ps is the pitch of the interference patterns formed with the diffraction grating, L2 is the distance from the X-ray window to the diffraction grating, and d is the distance from the diffraction grating to the interference patterns, and the direction in which the X-ray shielding members are arranged is orthogonal to the direction in which the emitting surfaces are arranged.

9. The X-ray imaging apparatus according to claim 1, wherein:
the target is formed by combining a plurality of first partial targets, each of the plurality of first partial targets including the plurality of emitting surfaces;
the plurality of emitting surfaces are made of a material that converts energy of the electron beams into X rays;
the plurality of first partial targets are arranged in the direction perpendicular to the direction in which the emitting surfaces are arranged in each of the plurality of first partial targets; and
the plurality of emitting surfaces are arranged with a pitch P0 between the emitting surfaces expressed by an equation: $P0=n \times Ps \times (L/d)$, where n is an arbitrary positive integer, Ps is the pitch of the interference patterns formed with the diffraction grating, L is the distance from the target to the diffraction grating, and d is the distance from the diffraction grating to the interference patterns.

10. The X-ray imaging apparatus according to claim 9, wherein:
the target includes the plurality of first partial targets and a plurality of second partial targets whose conversion rate for converting the energy of the electron beams into X rays is lower than the plurality of first partial targets;
the plurality of first partial targets and the plurality of second partial targets are arranged in the direction perpendicular to the direction in which the pitches between the emitting surfaces are arranged in each of the plurality of first partial targets; and
at least the plurality of first partial targets are arranged with the pitch P0 expressed by the equation: $P0=n \times Ps \times (L/d)$.

11. The X-ray imaging apparatus according to claim 9, wherein the direction in which the emitting surfaces are arranged in the target intersects with the direction in which the emitting surfaces are arranged in each of the plurality of first partial targets and also intersects with the direction in which the plurality of first partial targets are arranged.

12. The X-ray imaging apparatus according to claim 1, wherein the bright portions of the plurality of interference patterns partially overlap each other and the dark portions of the plurality of interference patterns partially overlap each other.

13. An X-ray computed tomography imaging system for obtaining a tomographic image of a specimen, comprising:
the X-ray imaging apparatus according to claim 1; and
a computer configured to obtain a tomographic image of the specimen on the basis of a plurality of phase images of the specimen generated by imaging the specimen from a plurality of different directions with the use of the X-ray imaging apparatus.

14. An X-ray source used in an X-ray imaging apparatus which comprises: an X-ray source including an electron source and a target, the target having a plurality of projections, each of the plurality of projections having an emitting surface; a diffraction grating configured to diffract X rays emitted from the X-ray source; and a detector configured to detect the X rays diffracted by the diffraction grating, wherein electron beams output from the electron source are incident on the emitting surfaces of the plurality of projections so that X rays are emitted from the emitting surfaces and are output to the diffraction grating, the X rays emitted from the emitting surfaces are diffracted by the diffraction grating so as to form a plurality of interference patterns, the plurality of projections are arranged such that bright portions of the plurality of interference patterns overlap each other and such that dark portions of the plurality of interference patterns overlap each other, and distances from the plurality of emitting surfaces to the diffraction grating are equal to each other.

* * * * *